United States Patent
Li et al.

(10) Patent No.: US 9,128,089 B1
(45) Date of Patent: Sep. 8, 2015

(54) AFLATOXIN M1 NANOBODY 2014AFM-G2

(71) Applicant: OILCROPS RESEARCH INSTITUTE OF CHINESE ACADEMY OF AGRICULTURE SCIENCES, Wuhan, Hubei (CN)

(72) Inventors: Peiwu Li, Hubei (CN); Ting He, Hubei (CN); Qi Zhang, Hubei (CN); Zhaowei Zhang, Hubei (CN); Xiaoxia Ding, Hubei (CN)

(73) Assignee: OILCROPS RESEARCH INSTITUTE OF CHINESE ACADEMY OF AGRICULTURE SCIENCES, Wuhan, Hubei (CN)

( * ) Notice: Subject to any disclaimer, the term of this patent is extended or adjusted under 35 U.S.C. 154(b) by 0 days.

(21) Appl. No.: 14/667,206

(22) Filed: Mar. 24, 2015

(30) Foreign Application Priority Data

Mar. 28, 2014 (CN) .......................... 2014 1 0121773

(51) Int. Cl.
*G01N 33/53* (2006.01)
*A61K 51/10* (2006.01)
*G01N 33/569* (2006.01)
*C07K 16/14* (2006.01)

(52) U.S. Cl.
CPC .......... *G01N 33/56961* (2013.01); *C07K 16/14* (2013.01); *C07K 2317/565* (2013.01); *C07K 2317/569* (2013.01); *G01N 2333/38* (2013.01); *G01N 2469/10* (2013.01)

(58) Field of Classification Search
None
See application file for complete search history.

(56) References Cited

FOREIGN PATENT DOCUMENTS

CN          102219853 A      10/2011

OTHER PUBLICATIONS

Wang Yan-ru et al., "Characterization of a Phage-Displayed Nanobody Imitating Aflatoxin Antigen", Scientia Agricultura Sinica, 2014, 685-695, 47(4).

*Primary Examiner* — Shafiqul Haq
*Assistant Examiner* — Carmencita M Belei
(74) *Attorney, Agent, or Firm* — Locke Lord LLP; Tim Tingkang Xia, Esq.

(57) ABSTRACT

Aflatoxin M1 nanobody 2014AFM-G2 has the amino acid sequence of SEQ ID NO:7, and is encoded by the gene sequence of SEQ ID NO:8. The aflatoxin M1 nanobody 2014AFM-G2 obtained via screening has the properties of tolerance to organic reagents, tolerance to high temperature, tolerance to acids and bases and the like, and good stability. The aflatoxin M1 nanobody 2014AFM-G2 has 50% inhibiting concentration $IC_{50}$ to aflatoxin M1 of 0.208 ng/mL, and has cross reaction rates with aflatoxin B1, B2, G1, G2 are 9.43%, 5.93%, 4.87% and 6.17%, respectively.

5 Claims, No Drawings

SEQUENCE LISTING

```
<160> NUMBER OF SEQ ID NOS: 13

<210> SEQ ID NO 1
<211> LENGTH: 8
<212> TYPE: PRT
<213> ORGANISM: Vicugna vicugna

<400> SEQUENCE: 1

Gly Arg Thr Phe Ser Ser Tyr Ala
1               5

<210> SEQ ID NO 2
<211> LENGTH: 8
<212> TYPE: PRT
<213> ORGANISM: Vicugna vicugna

<400> SEQUENCE: 2

Val Asn Trp Ser Gly Arg Arg Thr
1               5

<210> SEQ ID NO 3
<211> LENGTH: 14
<212> TYPE: PRT
<213> ORGANISM: Vicugna vicugna

<400> SEQUENCE: 3

Ala Ala Gly Lys Asp Gly Ser Tyr Tyr Gly Ala Pro Asp Tyr
1               5                   10

<210> SEQ ID NO 4
<211> LENGTH: 24
<212> TYPE: DNA
<213> ORGANISM: Vicugna vicugna

<400> SEQUENCE: 4
```
ggacgcacct tcagtagcta tgcc                                            24

<210> SEQ ID NO 5
<211> LENGTH: 24
<212> TYPE: DNA
<213> ORGANISM: Vicugna vicugna

<400> SEQUENCE: 5
gttaactgga gtggtcgccg caca                                            24

<210> SEQ ID NO 6
<211> LENGTH: 42
<212> TYPE: DNA
<213> ORGANISM: Vicugna vicugna

<400> SEQUENCE: 6
gcagccggga aggatggtag ttactatggc gctcctgact ac                        42

<210> SEQ ID NO 7
<211> LENGTH: 130
<212> TYPE: PRT
<213> ORGANISM: Vicugna vicugna

<400> SEQUENCE: 7

Gln Leu Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
        35                  40                  45

Ala Val Val Asn Trp Ser Gly Arg Arg Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Asn Cys
                85                  90                  95

Ala Ala Gly Lys Asp Gly Ser Tyr Tyr Gly Ala Pro Asp Tyr Trp Gly
            100                 105                 110

Gln Gly Thr Gln Val Thr Val Ser Ser Glu Pro Lys Thr Pro Lys Pro
        115                 120                 125

Gln Asp
    130

<210> SEQ ID NO 8
<211> LENGTH: 390
<212> TYPE: DNA
<213> ORGANISM: Vicugna vicugna

<400> SEQUENCE: 8
cagttgcagc tcgtggagtc tgggggagga ttggtgcagg ctgggggctc tctgagactc     60
tcctgtgcag cctctggacg cacctTcagt agctatgcca tgggctggtt ccgccaggct    120
ccagggaagg agcgtgagtt tgtagcagtc gttaactgga gtggtcgccg cacatactat    180
gcagactccg tgaagggccg attcaccatc tccagagaca cgccaagaa cacggtgtat    240 ctgcaaatga acagcctgaa acctgaggac acggctgttt ataactgtgc agccgggaag    300
gatggtagtt actatggcgc tcctgactac tggggccagg gacccaggt caccgtctcc    360 tcagaaccca agacaccaaa accacaagac                                     390

```
<210> SEQ ID NO 9
<211> LENGTH: 17
<212> TYPE: DNA
<213> ORGANISM: Artificial Sequence
<220> FEATURE:
<223> OTHER INFORMATION: Primer

<400> SEQUENCE: 9
atgcggccca gccggcc                                                        17

<210> SEQ ID NO 10
<211> LENGTH: 46
<212> TYPE: DNA
<213> ORGANISM: Artificial Sequence
<220> FEATURE:
<223> OTHER INFORMATION: Primer

<400> SEQUENCE: 10
gatcgggccc tgtggtggtg gtggtggtgt gcggccgccc gttttc                        46

<210> SEQ ID NO 11
<211> LENGTH: 41
<212> TYPE: DNA
<213> ORGANISM: Artificial Sequence
<220> FEATURE:
<223> OTHER INFORMATION: Primer

<400> SEQUENCE: 11
cggcgcacct gcggccgcat gggggtcttc gctgtggtgc g                             41

<210> SEQ ID NO 12
<211> LENGTH: 52
<212> TYPE: DNA
<213> ORGANISM: Artificial Sequence
<220> FEATURE:
<223> OTHER INFORMATION: Primer

<400> SEQUENCE: 12
tcctttctat gcggcccagc cggccatggc cccagktgca gctcgtggag tc                 52

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
cggcgcacct gcggccgcgt cttgtggttt tggtgtcttg gg                            42
```

AFLATOXIN M1 NANOBODY 2014AFM-G2

CROSS-REFERENCE TO RELATED APPLICATION

This non-provisional application claims priority under 35 U.S.C. §119(a) on Patent Application No. 201410121773.5 filed in P.R. China on Mar. 28, 2014, the entire contents of which are hereby incorporated by reference.

Some references, if any, which may include patents, patent applications and various publications, may be cited and discussed in the description of this invention. The citation and/or discussion of such references, if any, is provided merely to clarify the description of the present invention and is not an admission that any such reference is "prior art" to the invention described herein. All references listed, cited and/or discussed in this specification are incorporated herein by reference in their entireties and to the same extent as if each reference was individually incorporated by reference.

FIELD OF THE INVENTION

The present invention relates to aflatoxin M1 nanobody 2014AFM-G2.

BACKGROUND OF THE INVENTION

Aflatoxins are a group of highly toxic metabolites mainly produced by *Aspergillus flavus* and *Aspergillus parasiticus*. Aflatoxins are one category of most powerful carcinogenic substances ever discovered. 20 kinds of aflatoxins have now been found, which mainly include aflatoxin B1 ($AFB_1$), B2 ($AFB_2$), AFG, and M1 ($AFM_1$), etc. Among them, aflatoxin B1 is the most toxic and its toxicity is 10 folds of potassium cyanide and 68 folds of arsenic. Aflatoxin M1 ($AFM_1$) is a hydroxylated metabolite of AFB1. When the mammals ingest a feed contaminated by AFB1, AFB1 would be hydroxylated in vivo and secreted into milk. In general, after the animals ingest a food contaminated by AFB1, the discharge amount of aflatoxin M1 is 1%-3% of the intake amount of AFB1. A large number of researchers have conducted deep research on the toxicity and carcinogenicity of aflatoxin M1, and the research results motivate International Agency for Research on Cancer to change the carcinogenic rank of aflatoxin M1 from the category II carcinogenic substance to the category I carcinogenic substance. Aflatoxin M1 is stable in property and almost completely impossible to be destroyed even if it is subjected to pasteurization. Aflatoxin M1 is present in many dairy products. Since dairy products are the main source of infant foods, the problems about the aflatoxin M1 contamination have attracted worldwide attention and the amount of aflatoxin M1 is strictly limited in those dairy products. China belongs to heavily contaminated areas of aflatoxins, and therefore it is of important significance to intensify the detection especially the rapid detection of aflatoxin M1 in milk and dairy products to timely understand and grasp the health information about the milk and dairy products for ensuring the safety of food consumption in China.

The existing detection methods for aflatoxins include chemical analysis method, precision instrument analysis method and an immunological analysis method. Among them, the chemical analysis method is the most commonly used detection method for aflatoxins. The chemical analysis method does not need special instruments and equipment and can be carried out in ordinary laboratories, but it has the problems of large reagent consumption, tedious operation, severe interference by other components, poor accuracy, incapability of accurate quantification, great harm to experimenters and surrounding environment, and inapplicability to in-field rapid detection. The precision instrument analysis method includes fluorospectrophotometry and high performance liquid chromatography. The precision instrument analysis methods have high sensitivity and good accuracy, but the instruments therefor are expensive. Further, those methods require a high purification of aflatoxin samples, require tedious sample pretreatment procedures, are long time consumption, require high standard of experimental environment, and are difficult to realize rapid detection. Immunological analysis technology developed in recent years overcomes the disadvantages of the former two methods, has the advantages of strong specificity, high sensitivity, simple sample pretreatment, low cost, less contamination harm to experimenters and surrounding environment, applicability to in-field batch detection, etc., and has been applied in many fields such as food and medical treatment. Immunological analysis is based on the specificity between an antigen and an antibody and their reversible binding reactions. Using the antigen and the antibody as biochemical reactants to carry out qualitative and quantitative analysis on substances such as compounds, enzymes or proteins, has the advantages of good sensitivity and rapidness and simple operation. An anti-aflatoxin antibody must be prepared in advance in order to study and establish any immunological detection technique directed to aflatoxins.

Immunological analysis needs high-quality antibodies. With the development of antibody technology, recombinant antibodies are gradually applied in the aflatoxins detection field. Compared with traditional polyclonal antibodies and monoclonal antibodies, the recombinant antibodies have unique advantage in that recombinant antibodies are easily mass produced in protokaryotic expression system within a very short period of time with low production cost. Thus, recombinant antibodies have important application values for the low cost and large scale detection of aflatoxins, and can satisfy the growing demands for the production of aflatoxin antibodies. Nanobodies are variable region fragments of heavy chains of natural antibodies in an animal body of camelidae which are obtained by employing molecular biological means and can be specifically bound to antigens. Compared with traditional recombinant antibodies (such as single-chain antibodies), nanobodies have the advantages of small volume, good stability, tolerance to high temperature, tolerance to organic reagents, tolerance to acids and bases and the like. Currently, there is still no report related to aflatoxin M1 nanobodies.

SUMMARY OF THE INVENTION

In one aspect, the present invention relates to aflatoxin M1 nanobody 2014AFM-G2.

In one embodiment, an aflatoxin nanobody gene library is obtained by: extracting RNA from the blood of an alpaca after being immunized using aflatoxin M1 complete antigen, specifically amplifying the variable region genes of the heavy chains of IgG2 and IgG3 antibodies of the alpaca (i.e., the VHH gene) by RT-PCR method using the extracted RNA, then ligating the amplified gene to the pCANTAB 5E (his) vector, and transforming.

In one embodiment, the above described pCANTAB 5E (his) vector is constructed by the following method: using pCANTAB5E vector plasmid as the template, p5E SfiI-F: 5'-ATGCGGCCCAGCCGGCC-3'(Sfi I, SEQ ID NO:9) as the upstream primer and p5E N-P-H-R: 5'-GATCGGGC-CCTGTGGTGGTGGTGGTGGTGTGCGG CCGC- CCGTTTTC-3' (SEQ ID NO:10) as the downstream primer, PCR amplifying a DNA fragment between the SfiI and NotI on the pCANTAB5E vector plasmid and introducing a hexa-histidine tag after the Not I enzyme digestion site to obtain p5E-his fragments; then, firstly subjecting the p5E-his fragments to single enzyme digestion using SfiI followed by single enzyme digestion using PspoMI to obtain p5E-his (SfiI/PspoMI) cohesive termini, subjecting the pCANTAB5E vector plasmid to single enzyme digestion using SfiI followed by single enzyme digestion using Not I to obtain p5E (SfiI/NotI) cohesive termini; and finally ligating the p5E-his(SfiI/PspoMI) cohesive termini to the p5E (SfiI/NotI) cohesive termini to obtain the pCANTAB 5E (his) vector.

In one embodiment, the aflatoxin nanobody gene library is constructed by the following specific method: immunizing an alpaca with the aflatoxin M1 complete antigen, extracting RNA from the blood of the alpaca after being immunized, reversely transcribing as cDNA, designing specific primers, obtaining the variable region genes of the heavy chains of IgG2 and IgG3 antibodies in the blood of the alpaca (i.e., the VHH gene) via PCR amplification using cDNA as template, and then ligating the VHH gene to the pCANTAB 5E (his) vector followed by transformation to construct the aflatoxin nanobody gene library.

In the above-mentioned method, the termini of the specific primers should contain primer sequences for respectively introducing the homologous sequences of the vector pCANTAB 5E (his) at the two termini of the VHH gene which are designed according to the sequences adjacent to the cloning sites of the pCANTAB 5E (his) vector. The termini of each specific primer at least contain 15 bp homologous sites of the vector pCANTAB 5E (his) in order to respectively introduce at least 15 bp homologous sequences of the pCANTAB 5E (his) vector at the two termini of the VHH gene. The specific primers are:

```
                                              (SEQ ID NO: 11)
R1: 5'-CGG CGC ACC TGC GGC CGCATGGGGGTCTTCGCTGTGGT
GCG-3', (SEQ ID NO: 12)
F:  5'-TCCTTTCTATGCGGCCCAGCCGGCCATGGCCCCAGKTGCAGCT
CGTGGAGTC-3';
or (SEQ ID NO: 13)
R2: 5'-CGG CGC ACC TGC GGC CGCGTCTTGTGGTTTTGGTGTCT
TGGG-3', (SEQ ID NO: 12)
F:  5'-TCCTTTCTATGCGGCCCAGCCGGCCATGGCCCCAGKTGCAGCT
CGTGGAGTC-3',
``` in which the primer sequences indicated by the underlined parts are sites homologous to the pCANTAB 5E (his) vector.

In the above-mentioned method, the reaction system for said PCR amplification is:

| | |
|---|---|
| 10 × Ex taq Buffer | 5 μl |
| 50 mM MgSO$_4$ | 2 μl |
| 10 mM dNTP | 1 μl |
| 10 mM F primer | 1 μl |
| 10 mM R1 primer (or R2 primer) | 1 μl |
| Ex taq DNA polymerase | 0.1 μl |
| cDNA template | 2 μl |
| ddH2O added up to the total system | 50 μl; |

The procedures for said PCR amplification are:
94° C. for 2 min;
94° C. for 30 s, 55° C. for 30 s, 68° C. for 1 min, amplification for 30 cycles;
68° C. for 5 min.

In this case, the ratio of the PCR amplification reaction times using R1 as the primer to the PCR amplification reaction times using R2 as the primer is 2:3.

In the above-mentioned method, ligating the VHH gene to the pCANTAB 5 E (his) vector includes: subjecting the pCANTAB 5 E (his) vector to double enzyme digestion using SfiI/NotI and then conducting in-fusion ligation with the VHH gene. The transformation includes: adding the foregoing ligated product to electrotransformation-competent cells of *Escherichia coli* TG1, mixing uniformly, performing electrotransformation under the electrotransformation conditions of 0.1 cm electrotransformation cuvette, 1.8 kV, 200Ω, and 25 μF, followed by immediately adding 2YT liquid medium to the electrotransformation cuvette, pipetting up and down, transferring, and reviving cells at 37° C. under slow shaking for 1 h.

In one aspect, the present invention relates to the application of the above-mentioned aflatoxin nanobody gene library in screening aflatoxin M1 nanobodies via a phage display method.

In the above-mentioned application, the phage display method for screening aflatoxin M1 nanobodies is embodied via the following technical solution: rescuing the successfully-constructed aflatoxin nanobody gene library by M13KO7 helper phage to the form displayed on the surface of capsid of the phage, followed by panning by an adsorption-elution method to screen the positive wells which can specifically bind aflatoxin M1 but not bind carrier protein BSA, then using an indirect competitive enzyme-linked immunosorbent assay (ELISA) method to detect the culture solution of the positive wells screened in the first step using aflatoxin M1 as a competitive source, selecting the clones having relatively high sensitivity, and finally screening and obtaining phage-displayed aflatoxin M1 nanobodies.

In one aspect, the present invention relates to aflatoxin M1 nanobody 2014AFM-G2, which has the amino acid sequence of SEQ ID NO:7, and is encoded by the gene sequence of SEQ ID NO:8. The amino acid sequences of the three complementary determining regions therein are: the amino acid sequence of CDR1 as shown in SEQ ID NO:1, the amino acid sequence of CDR2 as shown in SEQ ID NO:2, and the amino acid sequence of CDR3 as shown in SEQ ID NO:3, respectively. The encoding gene sequences of the three complementary determining regions are: the encoding gene sequence of CDR1 as shown in SEQ ID NO:4, the encoding gene sequence of CDR2 as shown in SEQ ID NO:5, and the encoding gene sequence of CDR3 as shown in SEQ ID NO:6, respectively.

In one aspect, the present invention relates to application of the above-mentioned aflatoxin M1 nanobody 2014AFM-G2 in ELISA detection of aflatoxin M1.

Certain embodiments of the present invention, among other things, have the following beneficial advantages.

(1) The construction method of the aflatoxin nanobody gene library described in the present invention is simple. The aflatoxin M1 nanobody 2014AFM-G2 obtained via screening has the properties of tolerance to organic reagents, tolerance to high temperature, tolerance to acids and bases, and good stability.

(2) The aflatoxin M1 nanobody 2014AFM-G2 provided by the present invention has 50% inhibiting concentration IC$_{50}$ to aflatoxin M1 of 0.208 ng/mL, and its cross reaction rates with aflatoxins B1, B2, G1, and G2 are 9.43%, 5.93%, 4.87% and 6.17%, respectively.

(3) The aflatoxin M1 nanobody 2014AFM-G2 provided by the present invention can be applied in ELLSA detection of aflatoxin M1 and can effectively reduce the interference by other ingredients such as the organic reagents in the extracting solution of the sample, thus improving the detection accuracy.

(4) The aflatoxin M1 nanobody 2014AFM-G2 provided by the present invention is expressed by prokaryote *Escherichia coli*, and therefore the production cost of the antibody can be effectively reduced.

DETAINED DESCRIPTION OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprising", "including", "carrying", "having", "containing", "involving", and the like are to be understood to be open-ended, i.e., to mean including but not limited to.

Example 1

Construction of an Aflatoxin Nanobody Gene Library

1. Immunization of Animals

One male alpaca of 2 years old was purchased and immunized with the aflatoxin M1 complete antigen (AFM$_1$-BSA, Sigma-Aldrich Corporation). 200 µg of aflatoxin M1 complete antigen was emulsified with Freund's incomplete adjuvant, and subcutaneously injected to the alpaca at multiple points. The alpaca was immunized in an interval of 2 weeks. Blood was sampled intravenously from the alpaca 7-10 days after each immunization, and serum titer was determined using an indirect ELISA method. After selecting an immunization with the highest titer, 10 mL of blood was sampled for extracting the total RNA.

2. Construction of a cDNA Library (1) Extraction of the total RNA: after selecting an immunization with the highest serum titer in the alpaca, and 7-10 days after immunization, 10 mL of blood was sampled intravenously from the alpaca for extracting total RNA: the total RNA was extracted from the blood of the alpaca using LeukoLOCK Total RNA Isolation System of Life Technologies.

(2) Synthesis of cDNA: using the total RNA obtained in step (1) as the template and oligo (dT)$_{15}$ as the primer, and performing reverse transcription according to the reverse transcriptase instruction of Promega Inc. to synthesize the first strand of cDNA to obtain the cDNA library.

3. Construction of the Aflatoxin Nanobody Gene Library (1) using the cDNA obtained in step 2 as the template, and R1, F or R2, F as primers, performing PCR amplification to obtain the variable region genes of the heavy chains of the antibodies of the alpaca, i.e., VHH genes taking cDNA 2 µl, 10×PCR Buffer 5 µl, MgSO$_4$ (50 mM) 2 µl, dNTP (10 mmol/L) 1 µl, F primers (10 µmol/L) 1 µl, R1 (or R2) primers (10 µmol/L) 1 µl, DNAase 0.1 µl, sterile purified water 37.9 µl, in total volume of 50 µl, vortexing uniformly, centrifuging briefly, performing PCR amplification reaction with the reaction conditions of: 94° C. denaturing for 2 min; followed by 30 cycles of 94° C. denaturing for 30 s, 55° C. annealing for 30 s, and 68° C. elongation for 1 min; and 68° C. elongation for 5 min. The primers are:

```
                                        (SEQ ID NO: 11)
R1: 5'-CGG CGC ACC TGC GGC CGCATGGGGGTCTTCGCTGTGGT
GCG-3', (SEQ ID NO: 13)
R2: 5'-CGG CGC ACC TGC GGC CGCGTCTTGTGGTTTTGGTGTCT
TGGG-3';

(SEQ ID NO: 12)
F:  5'-TCCTTTCTATGCGGCCCAGCCGGCCATGGCCCCAGKTGCAGCT
CGTGGAGTC-3',
``` in which the primer sequences indicated by the underlined parts are sites homologous to the vector pCANTAB 5E (his); 4 PCR amplification reactions were performed using R1, F as primers, and 6 PCR amplification reactions were performed using R2, F as primers. PCR products were separated by 0.7% agarose gel electrophoresis, and DNA fragments of 450 by size were recovered using purification kit.

(2) Construction of the pCANTAB 5E (his) vector: using pCANTAB5E vector plasmid as the template, p5E SfiI-F: 5'-ATGCGGCCCAGCCGGCC-3'(Sfi I, SEQ ID NO:9) as the upstream primer and p5E N-P-H-R: 5'-GATCGGGC-CCTGTGGTGGTGGTGGTGGTGTGCGGC-CGCCCGTTTTC-3' (SEQ ID NO:10) as the downstream primer, PCR amplifying a DNA fragment between the Sfi I and NotI on the pCANTAB5E vector plasmid to obtain p5E-his fragments. Then, firstly subjecting the p5E-his fragments to single enzyme digestion using SfiI followed by single enzyme digestion using PspoMI to obtain p5E-his(SfiI/PspoMI) cohesive termini, subjecting the pCANTAB5E vector plasmid to single enzyme digestion using SfiI followed by single enzyme digestion using Not I to obtain p5E (SfiI/NotI) cohesive termini. Finally ligating the p5E-his(SfiI/PspoMI) cohesive termini to the p5E (SfiI/NotI) cohesive termini to obtain the pCANTAB 5E (his) vector.

(3) Double Enzyme Digestion Treatment of pCANTAB 5 E (his):

SfiI single enzyme digestion: reaction solution was prepared according to the following system:

| | |
|---|---|
| pCANTAB 5 E (his) vector | 30 µl |
| SfiI | 1 µl |
| 10 × M Buffer | 10 µl |
| ddH$_2$O added up to the total system | 100 µl |

50° C. water bath for 2 h, followed by recovering using agarose gel DNA purification kit.

NotI enzyme digestion: reaction solution was prepared according to the following system:

| | |
|---|---|
| pCANTAB 5 E (his)SfiI product recovered via SfiI single enzyme digestion | 30 μl |
| NotI | 1 μl |
| 10 × H Buffer | 10 μl |
| ddH$_2$O added up to the total system | 100 μl |

37° C. water bath for 4 h, followed by recovering using agarose gel DNA purification kit.

(4) Ligation of the VHH Gene to the pCANTAB 5 E (his) Vector Treated Via Double Enzyme Digestion In-fusion ligation was performed according to the following system:

| | |
|---|---|
| pCANTAB 5 E (his) vector treated with SfiI/NotI double enzyme digestion | 120 ng |
| VHH gene | 40 ng |
| 5 × In-Fusion buffer | 2 μl |
| In-Fusion Enzyme | 1 μl |
| ddH$_2$O added up to the total system | 10 μl |

37° C. water bath for 15 min followed by placing into 50° C. water bath for 15 min, then immediately placing onto ice and keeping for 5 min, adding 40 μl TE buffer, recovering using agarose gel DNA purification kit, and storing at −20° C. for use.

(5) Electrotransformation of the Ligated Product

5 μl of the above ligated product was taken and added to 50 μl electrotransformation-competent cells of *E. coli* TG1 and mixed uniformly, followed by adding to prechilled 0.1 cm electrotransformation cuvette (Bio-RAD), placing on ice and keeping for 10 min, then placing on Bio-rad electrotransformer for performing electrotransformation under the electrotransformation conditions of 1.8 kV, 200Ω, and 25 μF, followed by immediately adding 1 mL 2YT liquid medium to the electrotransformation cuvette, pipetting up and down, transferring to a 15 mL sterilized clean shake tube, and reviving cells at 37° C. under slow shaking for 1 h. 2 μl of bacterial culture was taken and subjected to double dilution, followed by spreading onto LB-ampicillin plates, inverting, and culturing at 37° C. overnight, and calculating the library capacity by counting the number of colonies in the next day.

(6) Rescue of Aflatoxin Nanobody Gene Library:

The above-mentioned electrotransformation was performed ten times in total, the revived bacterial culture was entirely transferred to 200 mL SB medium and shaken at 37° C. under 250 rpm until OD$_{600}$ value was 0.5, and then 1mL helper phage M13KO7 with 1×10$^{12}$ pfu was added, followed by standing at 37° C. for 1 h, continuing to shake for 2 h, adding kanamycin to reach a final concentration of 70 μg/mL and shaking overnight. The next day, the overnight bacteria culture were centrifuged at 4° C. under 10,000 rpm for 15 min, the supernatant was transferred to a sterile centrifuge bottle, ¼ volume of 5×PEG/NaCl was added, followed by standing on ice for 2 h, centrifuging at 4° C. at 12,000 rpm for 20 min, and dissolving the pellets in 10 mL sterile resuspension solution (PBS buffer containing 1× protease inhibitor, 0.02% NaN$_3$ and 0.5% BSA) to obtain the rescued aflatoxin nanobody gene library.

Example 2

Screening and Sequencing of Aflatoxin M1 Nanobodies

1. Panning of Aflatoxin M1 Nanobodies

ELISA plates were coated with AFM$_1$-BSA (1 μg/well) and 3% of BSA-PBS solution (used as the negative control) respectively at 4° C. overnight. In the next day, the coating solutions were poured off, the plates were washed with PBST for 3 times, and blocked with 3% skimmed milk powder for 1 h. The plates were washed with PBST for 3 times, 50 μl of the above-mentioned rescued aflatoxin nanobody gene library was added to the wells coated with AFM$_1$-BSA, and incubated at 37° C. for 1 h. The plates were washed with PBST for 10 times, 100 μl 100 ng/mL AFM$_1$ solution was added to each well, and eluting is performed via shaking at room temperature (20° C.-30° C.) for 30 min. The eluate was transferred to the wells coated with 3% BSA-PBS solution and incubated at 37° C. for 1 h (removing non-specific adsorption). After incubation, the supernatant was taken to infect with 2 mL of TG1 bacterial culture which has grown to the logarithmic phase, the infection was allowed at 37° C. for 20 min, followed by respectively taking 1 μl and 10 μl infested bacterial culture and spreading onto LB-ampicillin plates. The LB-ampicillin plates were sitting in an incubator at 37° C. overnight, and the phage titer in the eluate was determined by counting the number of the colonies on the plates in the next day. Additionally, the remaining above-mentioned TG1 bacterial culture after infection was transferred to 6 mL SB medium, 1.5 μl 100 mg/mL ampicillin was added, and the mixture was shaken at 37° C. for 1 h. Then supplementing ampicillin to reach a final concentration of 50 μg/mL, and continuing to shake for 1 h, adding 1 mL of helper phage M13KO7 (1×10$^{12}$ pfu/mL), standing at 37° C. for 30 min, transferring to 100 mL SB medium, supplementing 46 μl ampicillin (100 mg/mL), continuing to shake for 2 h, adding kanamycin to reach a final concentration of 70 μg/mL, and shaking at 37° C. overnight. The next day, the bacterial culture was centrifuged under 10,000 rpm at 4° C. for 15 min, followed by transferring supernatant, adding ¼ volume of 5×PEG/NaCl solution, incubating on ice for 2 h, centrifuging under 12,000 rpm at 4° C. for 20 min, and dissolving the pellets with 1% BSA-PBS solution to obtain the amplified product of the first round of panning, which was used for the next round of panning. In the subsequent several rounds of panning, the concentrations of the coating antigen AFM$_1$-BSA were 0.5 μg/well, 0.1 μg/well, 0.05 μg/well, respectively, and the eluents were AFM$_1$ solutions of 500 ng/mL, 100 ng/mL, 50 ng/mL, respectively.

2. Identification of Positive Clones:

After 4 rounds of panning, 2 μl of eluate was taken and subjected to double dilution, followed by infecting TG1 bacterial culture which has grown to the logarithmic phase. The infected TG1 bacterial culture was spread onto LB-ampicillin plates. The plates were placed invertedly, and incubated at 37° C. overnight. The next day, 30 clones were randomly picked out, and each of the clones was transferred to 3 mL SB-ampicillin culture medium, and cultured at 37° C. for 6-8 h under shaking until OD$_{600}$ was about 0.6. The culture medium was added with 30 μl helper phage M13KO7 (1×10$^{12}$ pfu/mL), sit at 37° C. for 30 min, shaken for 2 h, added with kanamycin to reach a final concentration of 70 μg/mL, cultured under shaken overnight, and centrifuging in the next day under 10,000 rpm at 4° C. for 15 min to obtain the supernatant of the bacterial culture.

AFM$_1$-BSA was prepared using coating solution to reach a final concentration of 0.2 μg/ml. The prepared 0.2 μg/ml AFM$_1$-BSA was used to coat 96-well ELISA plate, with 100 μl in each well. Meanwhile another ELISA plate was taken, 32 wells of which were coated with 3% BSA, and the plate was coated at 4° C. overnight. In the next day, the coating solution was pouring off, the plates were washed with PBST for 3 times, and then blocked with 3% skimmed milk powder-PBS for 1 h. AFM$_1$ standard stock solution was taken and prepared into 100 ng/mL and 0 ng/mL working solutions using 10% methanol/PBS, and respectively added to the wells coated with AFM$_1$-BSA antigens, and then 50 μl of the above-mentioned supernatant of bacterial culture was added to each well. Each concentration of the working solutions was repeated for 3 times. 10% methanol/PBS and 50 μl of the above-mentioned supernatant of bacterial culture were added to the wells coated with BSA as the control, the plates were gently shaken and mixing uniformly, and placed at 37° C. incubator to allow reaction for 1 h. The plates were washed with PBST 10 times, and 100 μl of HRP/ANTI-M13 diluted with PBS in a ratio of 1:5000 was added to each well, and the plates were incubated at 37° C. for 1 h. The plates were washed with PBST 6 times, 100 μl freshly prepared TMB substrate solution was added to each well, and the plates were incubated at 37° C. for 15 min. 50 μl 2 mol/L H$_2$SO$_4$ was added to each well to terminate the reaction, and OD$_{450}$ values were measured using a plate reader. The positive phage clones were those did not adsorb BSA, while adsorbed AFM$_1$-BSA, and had competition upon the addition of aflatoxin. The wells having both relatively high absorbance value and sensitivity were chosen, so as to obtain the phage-displayed aflatoxin M1 nanobody 2014AFM-G2.

3. The Properties and Sequencing Analysis Results of the Aflatoxin M1 Nanobody 2014AFM-G2 were as Follows The antibody specificity of aflatoxin M1 nanobody 2014AFM-G2, described particularly using the cross reaction rate, was determined using the indirect competitive ELISA method. The test method was as follows: diluting five different standard stock solutions of $AFM_1$, $AFB_1$, $AFB_2$, $AFG_1$ and $AFG_2$ in gradient to ten different working concentrations using 10% methanol/PBS, determining using the indirect competitive ELISA method under the same conditions, sequentially drawing five competitive ELISA curves for the five aflatoxins, calculating the standard concentrations when the inhibition rate was 50%, which were represented by $IC_{50}$, and calculating cross reaction rates according to the following calculation formula: cross reaction rate (%)=($AFM_1$ $IC_{50}$/analogue $IC_{50}$)×100%, where the analogue was $AFB_1$, $AFB_2$, $AFG_1$ or $AFG_2$. The 50% inhibiting concentration $IC_{50}$ of aflatoxin M1 nanobody 2014AFM-G2 to aflatoxin M1 was 0.208 ng/mL, and the cross reaction rates with aflatoxin B1, B2, G1, and G2 were 9.43%, 5.93%, 4.87% and 6.17%, respectively. Therefore, the aflatoxin M1 nanobody 2014AFM-G2 was a specific nanobody against aflatoxin M1. It can be seen from tolerance tests that as compared with conventional murine source antibodies and rabbit source antibodies, the tolerance capability of aflatoxin nanobody 2014AFM-G2 to organic solvents was improved by 35%, and the tolerance to high temperature thereof was improved by 45%. Therefore, this nanobody can effectively reduce the interference of other ingredients such as the organic solvents in the extracting solution of the sample during detection, thus improving the detection sensitivity.

Meanwhile, the screened clonal bacterial culture containing aflatoxin M1 nanobody 2014AFM-G2 was sent to Shanghai Sunny Biotechnology Co., Ltd. to conduct sequencing analysis. The sequencing primer was phage vector universal primer R1: 5'-CCA TGA TTA CGC CAA GCT TTG GAG CC-3'. The obtained amino acid sequence of the aflatoxin M1 nanobody 2014AFM-G2 was shown in SEQ ID NO:7, the encoding gene sequence thereof was shown in SEQ ID NO:8, where the amino acid sequences of the three complementary determining regions were: the amino acid sequence of CDR1 as shown in SEQ ID NO:1, the amino acid sequence of CDR2 as shown in SEQ ID NO:2, the amino acid sequence of CDR3 as shown in SEQ ID NO:3, respectively; the encoding gene sequences of the three complementary determining regions were: the encoding gene sequence of CDR1 as shown in SEQ ID NO:4, the encoding gene sequence of CDR2 as shown in SEQ ID NO:5, and the encoding gene sequence of CDR3 as shown in SEQ ID NO:6, respectively.

Example 3

Preparation of Aflatoxin M1 Nanobody 2014AFM-G2

(1) TG1 bacterial culture capable of secreting aflatoxin M1 nanobody 2014AFM-G2 was obtained, DNA mini-extraction kit of Qiagen was used to extract plasmids. The extracted plasmids were transformed to HB2151 competent cells, and the transformed competent cells were spread onto LB-ampicillin plates.

(2) HB2151 colonies containing aflatoxin M1 nanobody 2014AFM-G2 plasmids were picked out and inoculated onto 100 mL SB-ampicillin liquid culture medium. The inoculated culture medium was cultured under 250 rpm at 37° C. until OD600=0.5-0.8, and 200 μl 0.5 M IPTG solution was added to the culture to induce overnight.

(3) The cultured medium after induction was centrifuged at 4° C. under 10,000 rpm for 15 min. The supernatant was removed carefully in a sterile operation platform, and the bacterial cell pellets were subjected to soluble protein extraction using an osmotic shock method to obtain the proteins from the supernatant. The proteins from the supernatant were filtered using a 0.22 μm filter membrane, and dialyzed in an equilibrium buffer (50 mM phosphate, 300 mM sodium chloride, 20 mM imidazole, pH7.4) overnight.

(4) His60 nickel column (Clontech Technology) was used to purify antibodies. Firstly, the nickel column was rinsed with 10 folds the column volume of an equilibrium buffer. The proteins of the supernatant dialyzed in step (3) were loaded to His60 nickel column (Clontech Technology) for antibody purification. Then the column was washed with 10 folds the column volume of a rinsing buffer (50 mM phosphate, 300 mM sodium chloride, 40 mM imidazole, pH7.4). Finally, the antibody 2014AFM-G2 was eluted with 10 folds the column volume of an elution buffer (50 mM phosphate, 300 mM sodium chloride, 300 mM imidazole, pH7.4). The eluates were collected and put into a dialysis bag, dialyzed and concentrated using 0.01 M, pH7.4 phosphate buffer for 2-3 days, fractionized and stored at −20° C. for use.

Example 4

Application of the Aflatoxin M1 Nanobody 2014AFM-G2

1. Sample Pretreatment:

10 mL milk (cow) was measured and loaded to a 50 mL centrifuge tube, and centrifuged under 3,500 g at 4° C. for 10 min. The milk fat portion of the upper layer, was discarded, and the middle portion was collected (a milk sample) to be directly used in detection via the indirect competitive ELISA method. 10 g milk powder was accurately weighed and dissolved in 50° C. preheated purified water, and added up to 100 mL. The 100 mL milk power solution was centrifuged under 3,500 g at 4° C. for 10 min. The milk fat portion of the upper layer was discarded, and the middle portion was collected (a milk powder sample) to be directly used in detection via the indirect competitive ELISA method.

2. Indirect Competitive Enzyme-Linked Immunosorbent Assay 0.25 µg/mL $AFM_1$-BSA solution was prepared using a coating buffer, and added to an ELISA microplate, 100 µL/well for each well. The plate was kept at 4° C. overnight. In the next day, the plate was rinsed with PBST for three times, and the microwells were blocked with 200 µL of 1.5% OVA dissolved in PBS. The reactions was allowed in an incubator at 37° C. for 1 h. The plate was rinsed with PBST for three times. 50 µL aflatoxin M1 nanobody 2014AFM-G2 (0.9 µg/mL) and 50 µL $AFM_1$ standard solution or sample to be tested were added to each well. Reaction was allowed at 37° C. for 1 h. The plate was rinsed with PBST for three times. 100 µL rabbit anti-E tag enzyme-labelled secondary antibody diluted with PBS in a ratio of 1:5000 was added to each well, and the reaction was performed at 37° C. for 1 hour. The plate was rinsed with PBST for six times, and 100 µl freshly-prepared TMB substrate solution was added to each well, and the plate was incubated at 37° C. for 15 min. 50 µL 2 M sulphuric acid was added to each well to terminate the reaction, and the absorbance value at 450 nm was immediately measured using a plate reader. The concentration of $AFM_1$ in the sample was calculated according to the measured absorbance value of the sample, and the recovery rate of the method was determined. The average recovery rates of the milk sample and the milk powder sample were 90.8% and 87.9%, respectively, which can meet the requirements for the accuracy for the method for detecting aflatoxins.

In summary, aflatoxin M1 nanobody 2014AFM-G2 can effectively recognize aflatoxin M1 and can be used in ELISA detection of aflatoxin M1, and it is of important significance for monitoring aflatoxin M1 in the dairy product safety field.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments are chosen and described in order to explain the principles of the invention and their practical application so as to activate others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

What is claimed is:

1. An aflatoxin M1 nanobody 2014AFM-G2, comprising the amino acid sequence of SEQ ID NO:7.

2. The aflatoxin M1 nanobody 2014AFM-G2 according to claim 1, encoded by the nucleic acid sequence of SEQ ID NO:8.

3. The aflatoxin M1 nanobody 2014AFM-G2 according to claim 1, wherein SEQ ID NO:7 comprises three complementary determining regions of:
   CDR1 consisting of the amino acid sequence of SEQ ID NO:1;
   CDR2 consisting of the amino acid sequence of SEQ ID NO:2; and
   CDR3 consisting of the amino acid sequence of SEQ ID NO:3.

4. The aflatoxin M1 nanobody 2014AFM-G2 according to claim 3, wherein
   the CDR1 is encoded by the nucleic acid sequence of SEQ ID NO:4;
   the CDR2 is encoded by the nucleic acid sequence of SEQ ID NO:5; and
   the CDR3 is encoded by the nucleic acid sequence of SEQ ID NO:6.

5. An enzyme-linked immunosorbent assay (ELISA) kit for the detection of aflatoxin M1 comprising the aflatoxin M1 nanobody 2014AFM-G2 of claim 1.

* * * * *